(12) United States Patent
Chakravarthy et al.

(10) Patent No.: US 10,286,226 B2
(45) Date of Patent: May 14, 2019

(54) PHOTOTHERAPY DEVICE FOR THE TREATMENT OF HYPERBILIRUBINEMIA

(71) Applicant: D-Rev: Design for the Other Ninety Percent, San Francisco, CA (US)

(72) Inventors: Jayanth Chakravarthy, Santa Clara, CA (US); Krista Donaldson, San Francisco, CA (US); Peter Russo, Oakland, CA (US); Mohan Sancheti, Redwood City, CA (US); Randy Schwemmin, San Francisco, CA (US); Garrett Spiegel, San Francisco, CA (US)

(73) Assignee: D-Rev: Design for the Other Ninety Percent, San Francisco, CA (US)

( * ) Notice: Subject to any disclaimer, the term of this patent is extended or adjusted under 35 U.S.C. 154(b) by 261 days.

(21) Appl. No.: 15/074,568

(22) Filed: Mar. 18, 2016

(65) Prior Publication Data

US 2016/0263396 A1    Sep. 15, 2016

Related U.S. Application Data

(63) Continuation of application No. PCT/US2014/055125, filed on Sep. 11, 2014.
(Continued)

(51) Int. Cl.
*A61N 5/06* (2006.01)
*G01J 1/04* (2006.01)
*G01J 1/44* (2006.01)

(52) U.S. Cl.
CPC .......... *A61N 5/0621* (2013.01); *G01J 1/0407* (2013.01); *G01J 1/44* (2013.01);
(Continued)

(58) Field of Classification Search
CPC .............. A61N 5/06; A61N 2005/0626; A61N 2005/0627; A61N 2005/0628;
(Continued)

(56) References Cited

U.S. PATENT DOCUMENTS

| 3,877,437 A | 4/1975 | Maitan et al. |
| 4,802,066 A | 1/1989 | Mori |

(Continued)

FOREIGN PATENT DOCUMENTS

| WO | WO-2008011885 A2 | 1/2008 |
| WO | WO-2009050213 A1 | 4/2009 |

OTHER PUBLICATIONS

International search report and written opinion dated Feb. 25, 2015 for PCT Application No. US2014/055125.

*Primary Examiner* — Ahmed Farah
(74) *Attorney, Agent, or Firm* — Wilson Sonsini Goodrich and Rosati, P.C.

(57) ABSTRACT

A phototherapy device for treating neonatal hyperbilirubinemia comprises a plurality of LEDs coupled to a support structure configured to absorb and dissipate heat generated by the LEDs without requiring a fan. The LEDs provide a uniform dose of radiation on a treatment surface of the subject over a distance range of 20 cm to 45 cm. The support structure can comprise a heat-conductive metal plate. The LEDs have an emission range of 400 nm to 520 and a light output intensity of at least 30 µW/cm2/nm and at most 65 µW/cm2/nm at the treatment surface. The device can be adjustably coupled to a mounting structure. Power supplied to the LEDs is adjustable based on the total number of hours of use of he LEDs, the intensity of the LED radiation, the distance between the LEDs and the treatment surface, and/or the tilt or orientation of the phototherapy device.

14 Claims, 9 Drawing Sheets

Related U.S. Application Data

(60) Provisional application No. 61/879,619, filed on Sep. 18, 2013.

(52) U.S. Cl.
CPC .............. *A61N 2005/0626* (2013.01); *A61N 2005/0633* (2013.01); *A61N 2005/0642* (2013.01); *A61N 2005/0652* (2013.01); *A61N 2005/0662* (2013.01); *A61N 2005/0667* (2013.01)

(58) Field of Classification Search
CPC ...... A61N 2005/063; A61N 2005/0635; A61N 2005/0642; A61N 2005/065; A61N 2005/0651; A61N 2005/0652; A61N 2005/0667
USPC ................. 607/88–91, 96, 112; 606/9–12
See application file for complete search history.

(56) References Cited

U.S. PATENT DOCUMENTS

| | | | |
|---|---|---|---|
| 5,339,223 A | 8/1994 | Kremenchugsky et al. | |
| 5,400,425 A | 3/1995 | Nicholas et al. | |
| 5,698,866 A | 12/1997 | Doiron et al. | |
| 5,792,214 A | 8/1998 | Larsson et al. | |
| 6,045,575 A | 4/2000 | Rosen et al. | |
| 6,290,713 B1 | 9/2001 | Russell | |
| 6,402,681 B1 | 6/2002 | McDonough et al. | |
| 6,443,978 B1 | 9/2002 | Zharov | |
| 6,464,714 B1 | 10/2002 | Mewissen et al. | |
| 6,464,715 B1 | 10/2002 | Gysens et al. | |
| 6,596,016 B1 * | 7/2003 | Vreman | A61N 5/0621 128/903 |
| 6,811,563 B2 | 11/2004 | Savage et al. | |
| 6,866,678 B2 | 3/2005 | Shenderova et al. | |
| 6,872,220 B2 | 3/2005 | Williams et al. | |
| 6,955,684 B2 | 10/2005 | Savage et al. | |
| 7,128,442 B2 | 10/2006 | Lee et al. | |
| 7,131,990 B2 | 11/2006 | Bansal et al. | |
| 7,147,653 B2 | 12/2006 | Williams et al. | |
| 7,210,817 B2 | 5/2007 | Lee et al. | |
| 7,304,201 B2 | 12/2007 | Holloway et al. | |
| 7,305,163 B2 | 12/2007 | Williams | |
| 7,479,664 B2 | 1/2009 | Williams | |
| D639,751 S | 6/2011 | Tucker et al. | |
| 8,026,528 B2 | 9/2011 | Williams | |
| 8,043,349 B2 | 10/2011 | Springer, Jr. | |
| 8,048,136 B2 | 11/2011 | Chung et al. | |
| 8,069,857 B2 | 12/2011 | Chung et al. | |
| 8,202,307 B2 | 6/2012 | Rodrigues et al. | |
| 8,246,666 B2 | 8/2012 | Pressler et al. | |
| 8,267,922 B2 | 9/2012 | Hodge et al. | |
| 8,337,538 B1 | 12/2012 | Ford | |
| 8,372,063 B2 | 2/2013 | Williams | |
| 2006/0089685 A1 | 4/2006 | Streibich et al. | |
| 2006/0100675 A1 | 5/2006 | Gardner | |
| 2006/0217787 A1 | 9/2006 | Olson et al. | |
| 2006/0278816 A1 | 12/2006 | Booty | |
| 2006/0293727 A1 | 12/2006 | Spooner et al. | |
| 2007/0027510 A1 | 2/2007 | Rodrigues et al. | |
| 2007/0032842 A1 | 2/2007 | Strong | |
| 2007/0208395 A1 | 9/2007 | Leclerc et al. | |
| 2007/0208397 A1 | 9/2007 | Gardner | |
| 2007/0239232 A1 | 10/2007 | Kurtz et al. | |
| 2008/0116401 A1 * | 5/2008 | Rice | A61N 5/0621 250/516.1 |
| 2008/0205033 A1 | 8/2008 | Born et al. | |
| 2008/0275533 A1 | 11/2008 | Powell | |
| 2009/0030489 A1 | 1/2009 | Asvadi et al. | |
| 2009/0030490 A1 | 1/2009 | Pipe et al. | |
| 2009/0068613 A1 | 3/2009 | Wang et al. | |
| 2010/0179469 A1 * | 7/2010 | Hammond | A61N 5/0603 604/20 |
| 2012/0078328 A1 | 3/2012 | Vancraeyenest et al. | |
| 2012/0104277 A1 | 5/2012 | Morren | |
| 2012/0280114 A1 * | 11/2012 | Rodrigues | A61N 5/0621 250/214.1 |
| 2012/0303099 A1 | 11/2012 | D'Ambrosio et al. | |

* cited by examiner

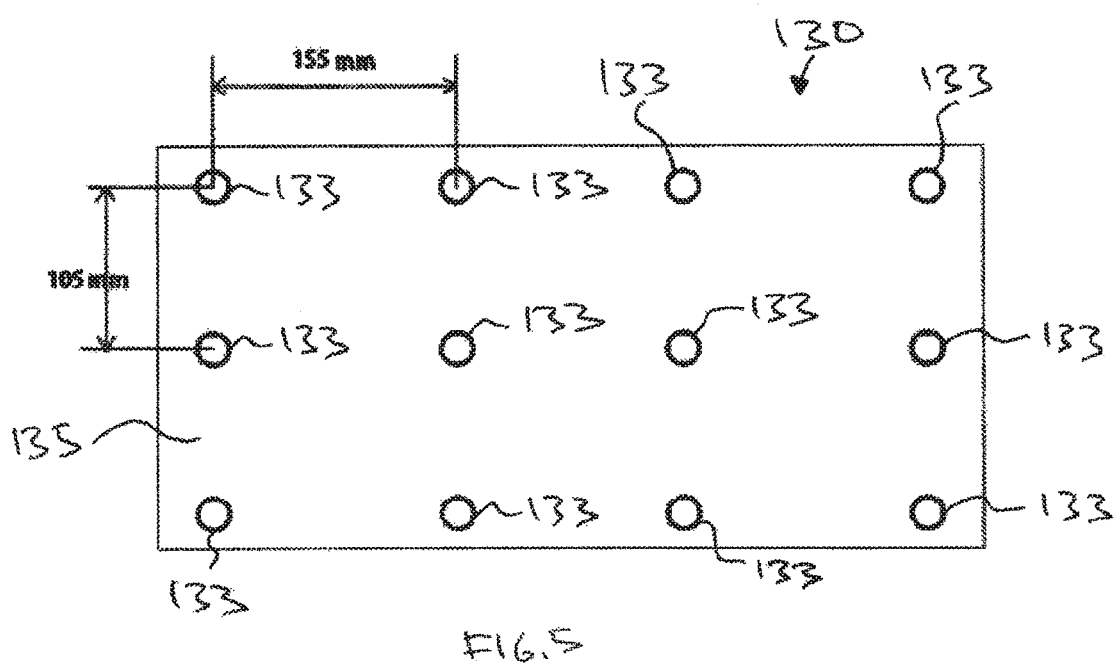

PHOTOTHERAPY DEVICE FOR THE TREATMENT OF HYPERBILIRUBINEMIA

CROSS REFERENCE

This application is a continuation of PCT Application Number PCT/US2014/055125, filed on Sep. 11, 2014, which claims priority to U.S. Provisional Patent Application Ser. No. 61/879,619, filed on Sep. 18, 2013, entitled "PHOTOTHERAPY DEVICE FOR THE TREATMENT OF HYPERBILIRUBINEMIA", the entire disclosure of which is incorporated herein by reference.

BACKGROUND OF THE INVENTION

The present disclosure relates generally to medical devices, systems, and methods. More specifically, the present disclosure relates to medical devices, systems, and methods for phototherapy to treat disorders such as hyperbilirubinemia and jaundice in infants.

Phototherapy typically involves shining light onto a patient's skin and is a promising clinical tool for the treatment of many conditions including affective disorder, sleep disorders, and skin disorders such as herpes, psoriasis, acne, and even skin cancer. Phototherapy is particularly promising in the treatment of neonatal hyperbilirubinemia, also known as newborn jaundice.

Neonatal hyperbilirubinemia affects over 60% of newborns worldwide. Hyperbilirubinemia is caused by the accumulation of excess bilirubin in the blood, which can give the skin and sclera of the eye a characteristic yellow color. If left untreated, an infant with severe jaundice may sustain neurological damage or even die. The condition requires treatment in approximately 12% of all infants. Studies have estimated that over 6 million newborns with severe jaundice are not receiving adequate treatment.

Hyperbilirubinemia can be treated using phototherapy. In such phototherapy, an infant is exposed to light in a wavelength range corresponding to the peak absorption spectra for bilirubin (blue-green, 400 to 520 nm), Absorption of the light leads to the conformational and structural isomerization of bilirubin into soluble forms that can be easily eliminated through urine.

The effectiveness of such phototherapeutic treatment is contingent on several factors. These factors include the intensity and spectrum of the delivered light, the surface area coverage of the delivered light, and the duration of light delivery. Existing devices are typically expensive, difficult to maintain, and often ineffective in low-income countries where the unmet need for jaundice treatment is the greatest. Thus, there is a need for high-performance phototherapy devices that are designed for extreme affordability. Also, illumination sources such as fluorescent bulbs, incandescent bulbs, fiber optic emitters, and LEDs are typically found in conventional phototherapy devices. Many of these illumination sources are not optimized for intensity, surface area coverage, maintenance, and costs.

The following literature publications may be of interest: "Light-Emitting Diodes: A Novel Light Source for Phototherapy" by Vreman et al, (1998), "An Evaluation of the Characteristics and Performance of Neonatal Phototherapy Equipment" by Dicken et al. (2000), "Treatment of Jaundice in Low Birthweight Infants" by Maisels et al. (2003), "A Prospective Randomized Controlled Study of Phototherapy Using Blue and Blue-Green Light-Emitting Devices, and Conventional Halogen-Quartz Phototherapy" by Seidman et al. (2003), and "Phototherapy: Current Methods and Future Directions" by Vreman et al. (2004).

The following patents and patent publications may be of interest: PCT Publication Nos. WO2008/011885 and WO2009/050213; U.S. Patent Application Publication Nos. 2006/0089685, 2006/0100675, 2006/0217787, 2006/0278816, 2006/0293727, 2007/0032842, 2007/0208395, 2007/0208397, 2007/0239232, 2008/0116401, 2008/0205033, 2008/0275533, 2009/0030490, 2009/0068613, 2010/0179469, 2012/0078328, 2012/0104277, and 2012/0280114; and, U.S. Pat. Nos. D639751, 3,877,437, 4,802,066, 5,339,223, 5,400,425, 5,698,866, 5,792,214, 6,045.575, 6,290,713, 6,402,681, 6,443,978, 6,464,714, 6,464,715, 6,596,016, 6,811,563, 6,866,678, 6,872,220, 6,955,684, 7,128,442, 7,131,990, 7,147,653, 7,210,817, 7,304,201, 7,305,163, 7,479,664, 8,026,528, 8,043,349, 8,048,136, 8,069,857, 8,202,307, 8,246,666, 8,267,922, 8,337,538, and 8,372,063.

SUMMARY OF THE INVENTION

The present disclosure provides devices, systems, and methods for treating neonatal hyperbilirubinemia with phototherapy using LEDs configured to optimize such phototherapy. A phototherapy device according to many embodiments may comprise a plurality of LEDs configured to provide a uniform intensity light at a specified distance range. The specific number of LEDs used may be minimized to a number sufficient to provide such uniform intensity. One or more lenses or filters may be provided for the phototherapy devices. The LED(s) may be provided on a light source or lamp head mounted on a stand or mounting structure, which may be coupled to a support for an infant patient to rest on. The LED(s) will typically have a long lifespan, such as 7.6 years assuming 18 hours of usage per day such that bulb replacement for the phototherapy device is often unnecessary. Thus, a single phototherapy device can treat up to 1,042 infants assuming an average treatment time of 48 hours. The effectiveness of the LED(s) through this long lifespan can be maintained by discretely increasing one or more of current and power supplied to the one or more LEDs as their total light hours increase and the LEDs naturally decay. The power or current supplied to the LED(s) can also be adjusted in response to changes in the tilt or orientation of the phototherapy device or lamp head. The LED(s) are typically coupled to a heat dissipating base or support structure to minimize overheating without requiring the use of a fan, thus lowering the need for additional parts. The disclosure therefore provides cost-effective (e.g., less than 400 USD per device) and long-lasting devices, systems, and methods for phototherapy.

Aspects of the disclosure provide a phototherapy device for the treatment of a subject. The device comprises one or more LEDs and a base or support structure for coupling to and supporting the one or more LEDs. The one or more LEDs are configured to provide a uniform dose of radiation on a treatment surface of the subject over a distance range. The support structure is configured to absorb and dissipate heat generated by the one or more LEDs to minimize overheating generally without requiring the use of a fan. The power supplied to the one or more LEDs may be adjustable by one or more of resistor placement and pulse-width modulation (PWM). The one or more LEDs may comprise a plurality of LEDs distributed over the support structure, where the power supplied to each LED may be independently adjustable. The support structure may comprise a heat-conductive metal plate.

The desired distance range over which the uniform dose of radiation produced may be a range from 20 cm to 50 cm. The distance range may be from about 10 cm to 30 cm, 20 cm to 30 cm, or 20 cm to 45 cm, for example. The one or more LEDs may have an emission range of 400 nm to 520 nm, preferably 430 nm to 490 nm or 475 nm to 500 nm, more preferably 445 nm to 470 nm or 450 nm to 470 nm, and even more preferably 450 nm to 465 nm. The one or more LEDs may be configured to output one or more of at least 30 $\mu W/cm^2/nm$, preferably at least 35 $\mu W/cm^2/nm$, and at most 65 $\mu W/cm^2/nm$ over the distance range and across an emission range, e.g., 400 nm to 520 nm. The treatment surface may have an area of about 25 cm by 50 cm.

The phototherapy device may have additional components. The phototherapy device may further comprise a processor for controlling the power supplied to the one or more LEDs and/or their output. The phototherapy device may further comprise a display coupled to the processor for displaying one or more treatment parameters such as an intensity of the one or more LEDs, a wavelength of the one or more LEDs, a treatment time, a time of total use of the one or wore LEDs, a light meter reading, an accelerometer reading, and a checksum. The phototherapy device may further comprise a light meter for detecting an intensity of light from the one or more LEDs. The phototherapy device may further comprise one or more of an accelerometer for detecting an orientation of the phototherapy device and a distance meter to measure the distance between the LEDs and the treatment surface. Power supplied to the one or more LEDs can be adjusted in response to one or more of the detected orientation of the phototherapy device and the distance between the LEDs and the treatment surface. The phototherapy device may further comprise a timer or a memory to measure the total number of hours of use of the LEDs, and the power supplied to the LEDs can be increased as the total number of hours of use increases. As the total number of hours of use of an LED increases, the LED may become dimmer and so current and therefore power supplied to the LEDs may need to be gradually increased to maintain the light output intensity of the LEDs, increasing the effective lifespan of the phototherapy device. The phototherapy device may further comprise one or more focusing lenses coupled to each of the one or more LEDs. The phototherapy device may further comprise one or more filters coupled to each of the one or more LEDs. The one or more filters may be configured to have a transmission spectrum corresponding to an absorption spectrum of bilirubin. The phototherapy device may further comprise one or more LEDs having an emission range of about 550 nm to 650 nm, configured to illuminate the patient. These LEDs can be switched on together with or independently of the LEDs configured to provide the treatment radiation, and may be configured to automatically power off after a specified length of time.

Aspects of the disclosure also provide a light meter for measuring the intensity of radiation provided by a light source. The light meter may comprise one or more filters, a light sensor, and a circuit board. The one or more filters may be configured to have a transmission spectrum corresponding to a target range of wavelengths, for example an absorption spectrum of bilirubin. The light sensor is configured to detect radiation within a target range of wavelengths, and/or output a voltage corresponding to the detected radiation. The circuit board may have a calibration curve stored thereon, and the circuit board may use the calibration curve to convert the voltage output of the light sensor into an irradiance value. The light meter may be used as an independent unit, having its own display so that the irradiance value may be displayed. The light meter may also be connected to a mobile control device such as a cell phone via a connector port, such that the irradiance value is communicated to and displayed by the mobile device.

Aspects of the disclosure also provide a phototherapy system comprising a mounting structure and the phototherapy device discussed above which is coupled to the mounting structure. The phototherapy device may be adjustably coupled to the mounting structure. For example, the angle of the phototherapy device relative to the mounting structure may be adjusted. The mounting structure will typically be mobile, for example, by comprising a mounting structure base having one or more wheels for mobility. The mounting structure may comprise a height adjustable stand. The mounting structure may further comprise a height indicator that indicates the distance between the LEDs and the treatment surface. The height indicator may comprise a treatment height indicator to indicate the distance range, for example 20 cm-50 cm, of the phototherapy device. The height indicator may also comprise a distance meter having a distance sensor, such as an optical range finder, that may be configured to measure the distance between the LEDs and the treatment surface. The measured distance may be communicated to the processor of the phototherapy device to adjust the power supplied to the LEDs correspondingly. The system may further comprise a light intensity monitor or light meter, configured to measure the intensity of the radiation provided by the LED.

Aspects of the disclosure also provide a phototherapy system for the treatment of a subject. The system may comprise a phototherapy device comprising one or more LEDs configured to provide a uniform dose of radiation on a treatment surface of the subject over a distance range. The system may also comprise a light meter as discussed above, configured to measure the intensity of the radiation provided by the LEDs of the phototherapy device. The light meter may be stored with the phototherapy device in many ways. The phototherapy device may comprise a hook which may be engaged with an opening on the handle portion of the light meter, and/or a holster which may hold the light meter. The light meter may also be magnetically couplable with a surface of the phototherapy device. The light meter may be connected to the phototherapy device via a connector port, so the irradiance value from the light meter may be communicated to a processor of the phototherapy device and displayed by a display of the phototherapy device.

Aspects of the disclosure also provide a phototherapy device for the treatment of a subject. The device comprises one or more LEDs, a support structure, and a processor. The one or more LEDs are configured to provide a uniform dose of radiation on a treatment surface of the subject over a distance range. The support structure couples to and supports the one or more LEDs. The processor is configured to adjust the power supplied to the one or more LEDs, in response to one or more of a detected tilt or orientation of the phototherapy device, a distance between the LEDs and the treatment surface, and a total number of hours of use of the one or more LEDs. The orientation of the phototherapy device may be provided by an accelerometer of the phototherapy device. The distance between the LEDs and the treatment surface may be provided by a distance meter of the phototherapy device or of a mounting structure coupled to the phototherapy device. The phototherapy device may further comprise a display coupled to the processor, and the distance measured by the distance meter may be displayed by the display, The total number of hours of use of the LEDs may be provided by a timer or a memory of the phototherapy device. The support structure can be configured to absorb and dissipate heat generated by the one or more LEDs to minimize overheating without requiring the use of a fan.

Aspects of the disclosure also provide a phototherapy system comprising a phototherapy device having a processor to adjust the power supplied to the LEDs as described above, and a light meter as described above. The processor of the device can calculate the dose of radiation provided to a patient, based on one or more of the size of the exposed treatment surface, the distance between the LEDs and the treatment surface, the total number of hours of use of the LEDs, and the intensity of the radiation provided by the LEDs.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 shows a bottom view of an LED arrangement of the light emitting head unit of the phototherapy system of FIG. 1.

DETAILED DESCRIPTION OF THE INVENTION

The present disclosure provides devices, systems, and methods for treating neonatal hyperbilirubinemia with phototherapy using LEDs configured to optimize such phototherapy. A phototherapy device according to many embodiments may comprise a plurality of LEDs configured to provide a uniform intensity light at a specified distance range. The specific number of LEDs used may be minimized to a number sufficient to provide such uniform intensity. One or more lenses or filters may be provided for the phototherapy devices. The LED(s) may be provided on a light source mounted on a stand or mounting structure which may be coupled to a support for an infant patient to rest on.

Figure 1:
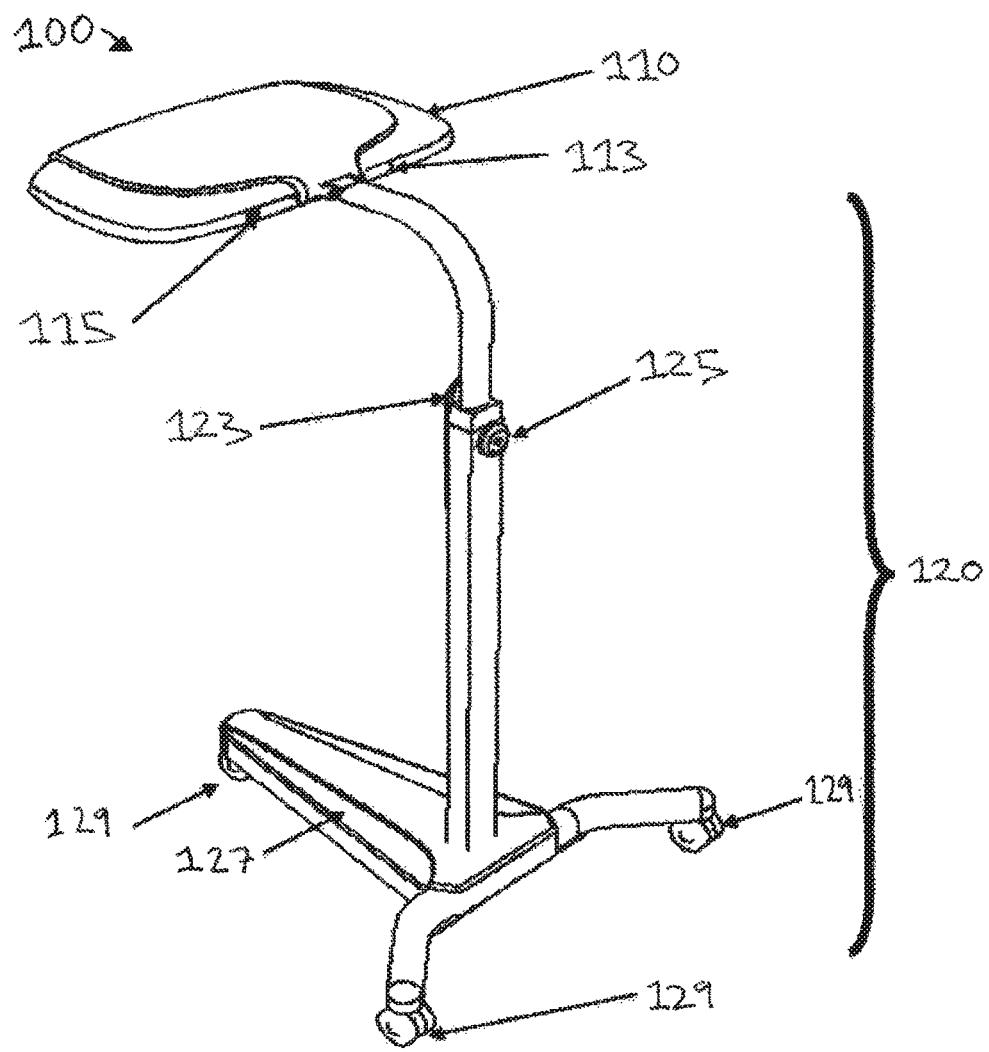
FIG. 1 shows a perspective view of a phototherapy system according to many embodiments.

FIG. 1 shows a perspective view of a phototherapy system 100. The phototherapy system 100 comprises a light emitting head unit or phototherapy device 110 for emitting therapeutic light and a mounting structure 120 on which the phototherapy device 110 is mounted. The mounting structure 120 can hold the phototherapy device 110 in place above, below, or otherwise near a subject or patient. For example, the mounting structure 120 may be clipped or fastened over a bassinet, incubator, or bed.

The height of the mounting structure 120 may be adjustable. As shown in FIG. 1, the mounting structure 120 may comprise a height indicator 123 and a height adjustment knob 125 for adjusting the height of the mounting structure 120. The height indicator 123 can facilitate aligning the phototherapy device 110 at a predetermined distance and height with respect to a subject. The indicator 123 may comprise a distance meter having a sensor, such as an optical range finder, to detect the distance between the phototherapy device and the treatment surface of the patient. The detected distance may be used as feedback to adjust the current input to the LED strings described below through pulse width modulation (PWM) as described below, to maintain an effective irradiance footprint at the treatment surface. The height indicator 123 may comprise a treatment height indicator to indicate optimum treatment height, for example, a sticker or an overhanging acrylic sheet. In operation, an infant patient or subject may be placed under the phototherapy device 110 and the height of the mounting structure 120 may be adjusted to align the phototherapy device 110 over the infant patient or subject. In exemplary embodiments, the height adjustment range may be from 110 cm to 160 cm. The device may be configured to be effective over a wide range of distances from the treatment surface of the patient, for example, within the range from about 10 cm to about 50 cm. In preferred embodiments, the effective distance range may be about 20 cm to 45 cm. The infant patient or subject or the phototherapy device 110 may be moved so that the therapeutic light emitted from the phototherapy device 110 is centered on the chest or abdomen of the infant patient or subject. An optimum distance from the infant patient or subject, such as a distance in the range from about 20 cm to 45 cm, may be indicated by the height indicator 123.

As shown in FIG. 1, the mounting structure 120 may comprise a base 127 optionally having wheels 129. The wheeled base 127 of the mounting structure 120 allows the phototherapy system 100 to be easily mobile. The wheels 129 may be locked to hold the mounting structure 120 and the phototherapy system 100 in place. In exemplary embodiments, the base 127 has dimensions of 71 cm in length, 71 cm in width, and 13 cm in depth.

As shown in FIG. 1, the phototherapy device 110 may comprise a power supply port 113 for supplying power to the phototherapy device 110 and an on/off switch 115 for switching one or more of the emission of the therapeutic light from the phototherapy device and the phototherapy device on and off.

Figure 2A:
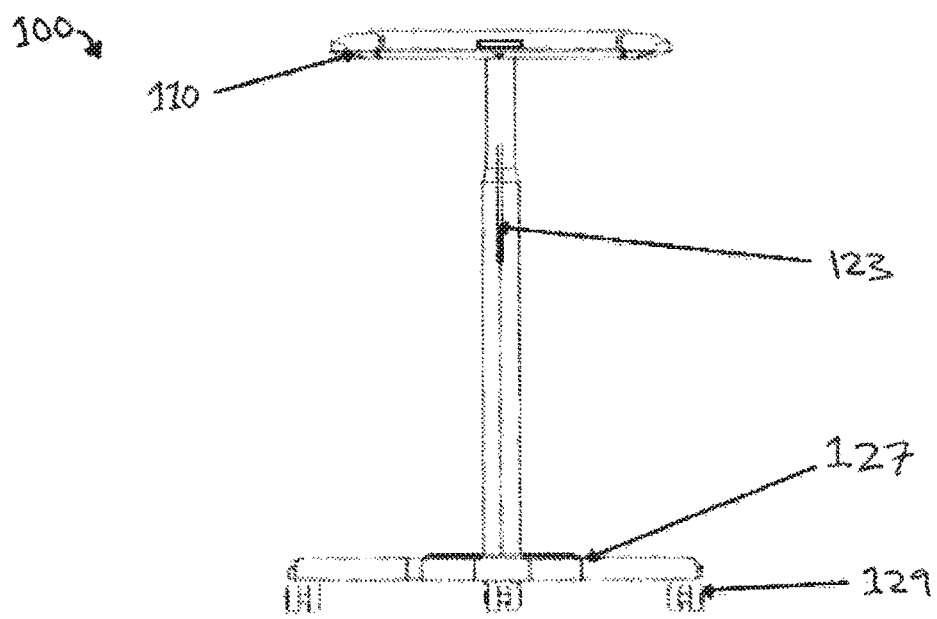
FIG. 2A shows a front view of the phototherapy system of FIG. 1.
Figure 2B:
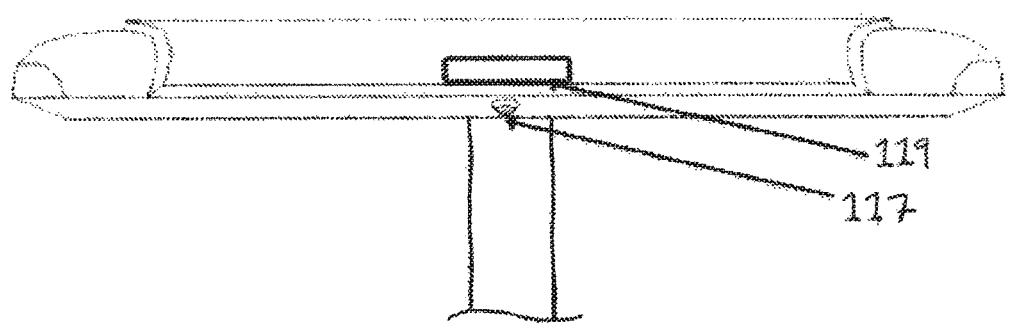
FIG. 2B shows a front view of the light emitting head unit of the phototherapy system of FIG. 1.

FIG. 2A shows a front view of the phototherapy system 100 and FIG. 2B shows a front view of the light emitting head unit or phototherapy device 110. As shown in FIG. 2B, the phototherapy device 110 may further comprise a reset button 117 and a display 119.

Figure 3A:
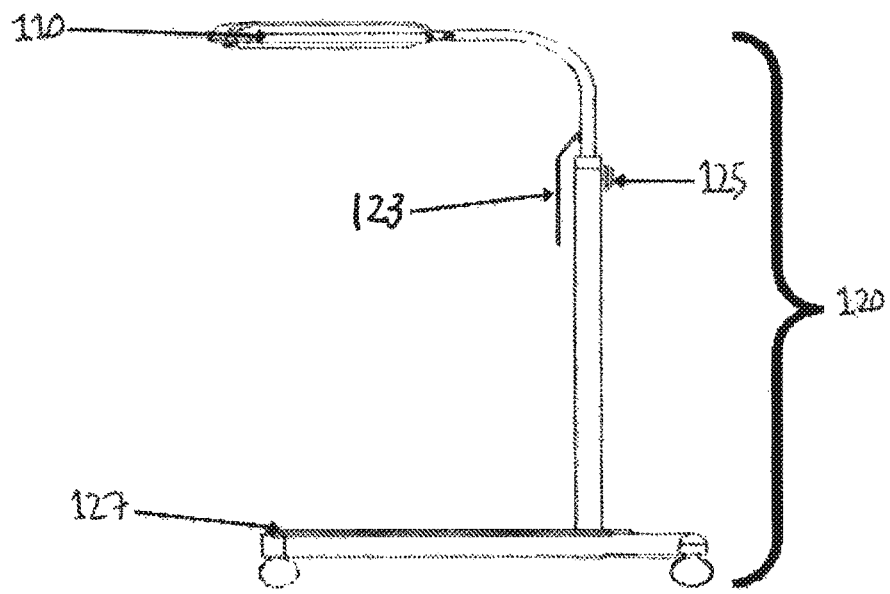
FIG. 3A shows a side view of the phototherapy system of FIG. 1.
Figure 3B:
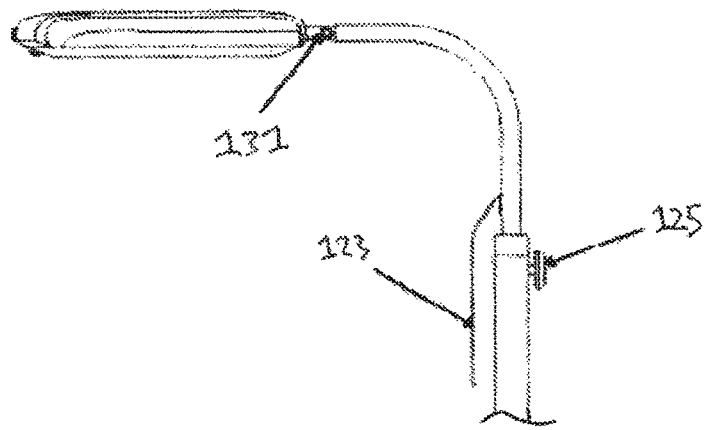
FIG. 3B shows a side view of the light emitting head unit of the phototherapy system of FIG. 1.

FIG. 3A shows a side view of the phototherapy system 100 and FIG. 3B shows a side view of the light emitting head unit or phototherapy device 110. As shown in FIG. 3B, the phototherapy device 110 may be coupled to the mounting structure 120 through an adjustable coupler or hinge 131.

Figure 4A:
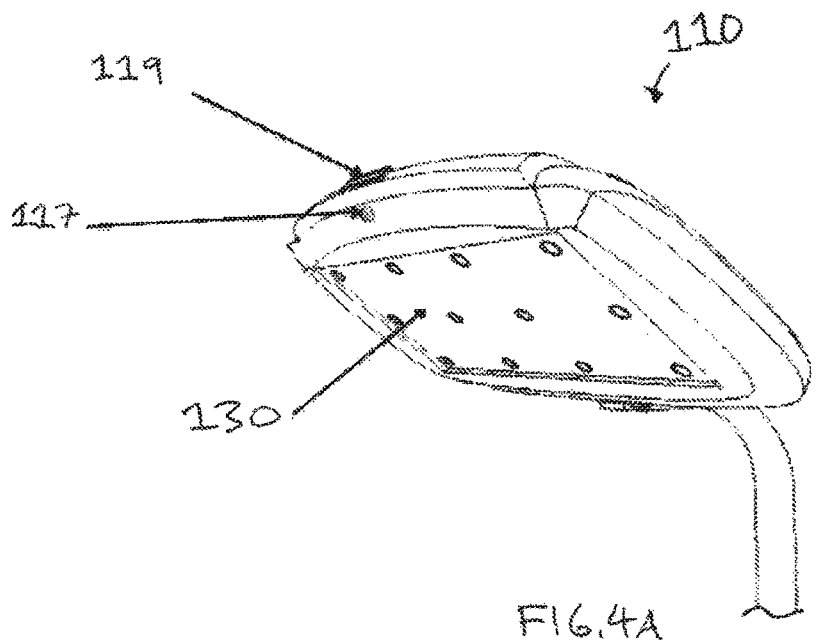
FIG. 4A shows a front, perspective view of the light emitting head unit of the phototherapy system of FIG. 1.
Figure 4B:
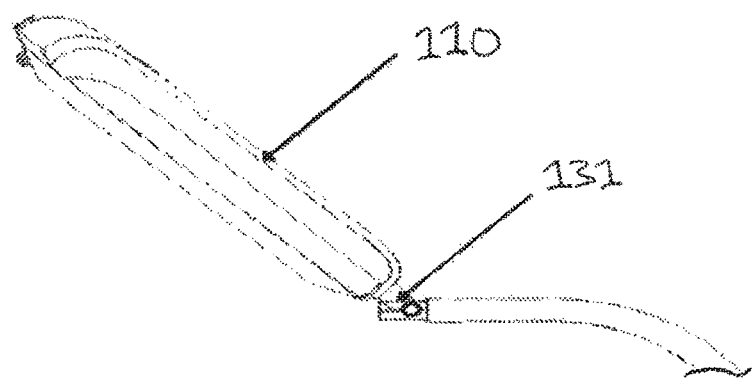
FIG. 4B shows a side view of the light emitting head unit of the phototherapy system of FIG. 1.
Figure 4C:
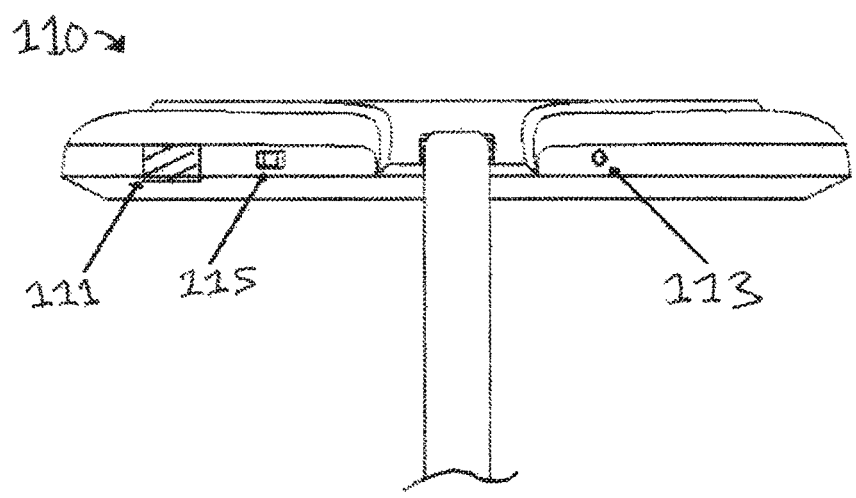
FIG. 4C shows a back view of the light emitting head unit of the phototherapy system of FIG. 1.
Figure 4D:
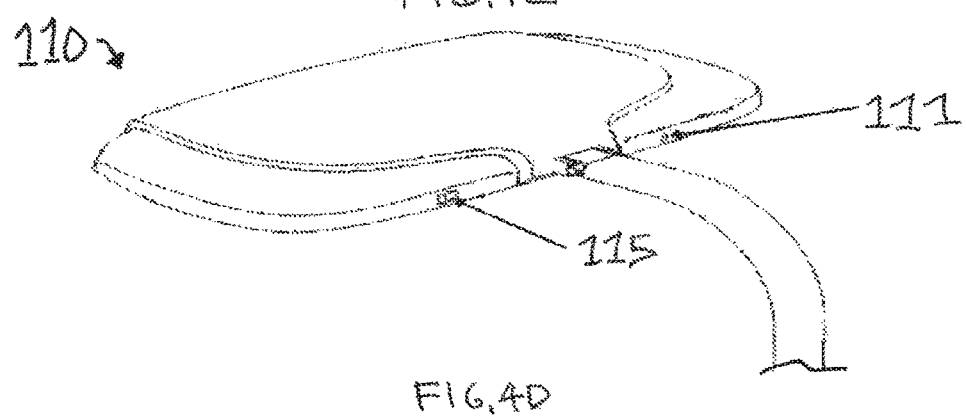
FIG. 4D shows a back, perspective view of the light emitting head unit of the phototherapy system of FIG. 1.

FIG. 4A shows a front, perspective view of the light emitting head unit or phototherapy device 110. As shown in FIG. 4A, the phototherapy device 110 may comprise an LED arrangement 130. FIG. 4B shows a side view of the light emitting head unit or phototherapy device 110. As shown in FIG. 4B, the angle of the phototherapy device 110 relative to the mounting structure 120 can be adjusted by rotating the phototherapy device 110 about the adjustable coupler or hinge 131. FIG. 4C shows a back view of the light emitting head unit or phototherapy device 110. FIG. 4C shows the power supply port 113 and on/off switch 115 of the phototherapy device 110. As shown in FIG. 4C, the phototherapy device 110 may further comprise an exhaust port 111 for venting heat out of the internal components of the phototherapy device 110. The exhaust port 111 may comprise a component of a cooling mechanism of the phototherapy device 110 which may include one or more fans or heatsinks. FIG. 4D shows a back, perspective view of the light emitting head unit or phototherapy device 110. The light head unit or phototherapy device 110 may further comprise a replaceable line fuse in the back of the unit.

FIG. 5 shows a bottom view of the LED arrangement 130 of the light emitting head unit or phototherapy device 110. As shown in FIG. 5, the LED arrangement 130 may comprise a plurality of individual LEDs 133 mounted on a substrate or support structure 135. The individual LEDs 133 may be spaced apart from one another by a first distance in a first direction (e.g., 155 mm) and a second distance in a second direction (e.g., 105 mm) to form a matrix. The individual LEDs 133 may be spaced apart front one another to diffuse or alter the concentration of light transmission from the individual LEDs 133. The LED arrangement 130 can provide a uniform and precise phototherapeutic light exposure on a subject. The on/off switch 115 of the phototherapy device 110 may be used to turn one or more of the device 110 and the LED arrangement on or off, e.g., turn the power supplied to the device 110 on or off, and in some embodiments to adjust the intensity and/or emission wavelengths of the LEDs. The phototherapy device 110 may further comprise a processor or programmable microcontroller and comparator circuit and optionally a memory module for adjusting the LEDs 133 and their lenses. Control circuitry may be provided so that the LEDs 133 may be turned on or off while a supply of power is maintained to the control and operational circuitry. In some embodiments, the LEDs 133 and their lenses may be commonly adjustable or separately adjustable to achieve a desired light emission pattern on a subject.

Each individual LED 133 may have a lens coupled thereto to focus, contour, diffuse, attenuate, alter, or otherwise manage the light emitted from the LED 133. These lenses may be fixed to each individual LED 133 or may be detachable from the individual LEDs 133. The individual LEDs 133 may emit light at the same wavelengths or different wavelengths from one another. The LEDs 133 will typically emit blue-green light at a range of 400 nm to 520 nm, preferably 430 to 490 nm, more preferably 445 nm to 470 nm, and even more preferably 450 nm to 465 nm, to isomerize bilirubin in a subject into soluble forms that can be easily eliminated through urine. Other wavelengths of light may instead be used as well. The LEDs 133 may also comprise LEDs emitting white or amber light in the range of about 550 nm to 650 nm, for use in observing the patient. The white-amber LEDs may be switched on together with or independently of the blue-green LEDs for treatment, and may be programmed to power off automatically after a specified length of time. The optimal distance between the subject, in particular the subject's chest and abdomen area, and the LED arrangement 130 may be in a range of about 20 cm to 45 cm. In some embodiments, a distance of about 20 cm is preferred. The arrangement of the individual LEDs 133 in combination with the lenses for the individual LEDs can form a light source array that achieves maximum coverage area of the subject using the minimum number of individual LEDs 133. Alternatively or in combination, a common lens may be provided for the individual lenses 133 of the LED arrangement 130. Combination of lenses may be provided to provide multiple treatment options.

Figure 6:
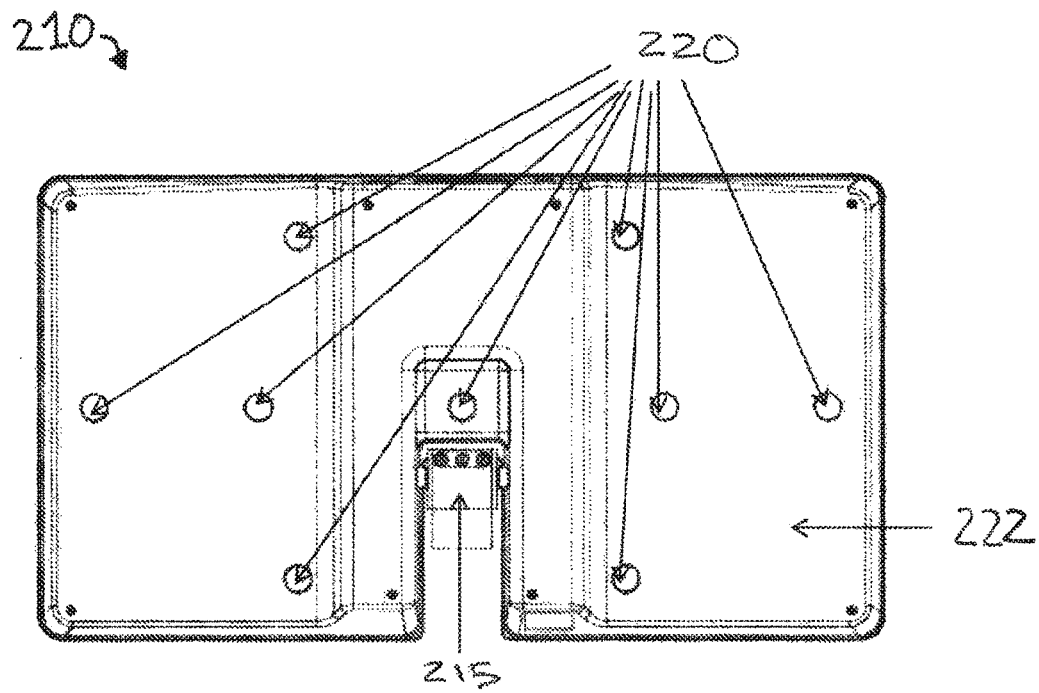
FIG. 6 is a bottom view of another light emitting head unit or phototherapy device according to many embodiments.

FIG. 6 is a bottom view of another light emitting head unit or phototherapy device 210 according to many embodiments. The light emitting head unit or phototherapy device 210 may be similar in many respects to the light emitting head unit or phototherapy device 110 described above.

Figure 7:
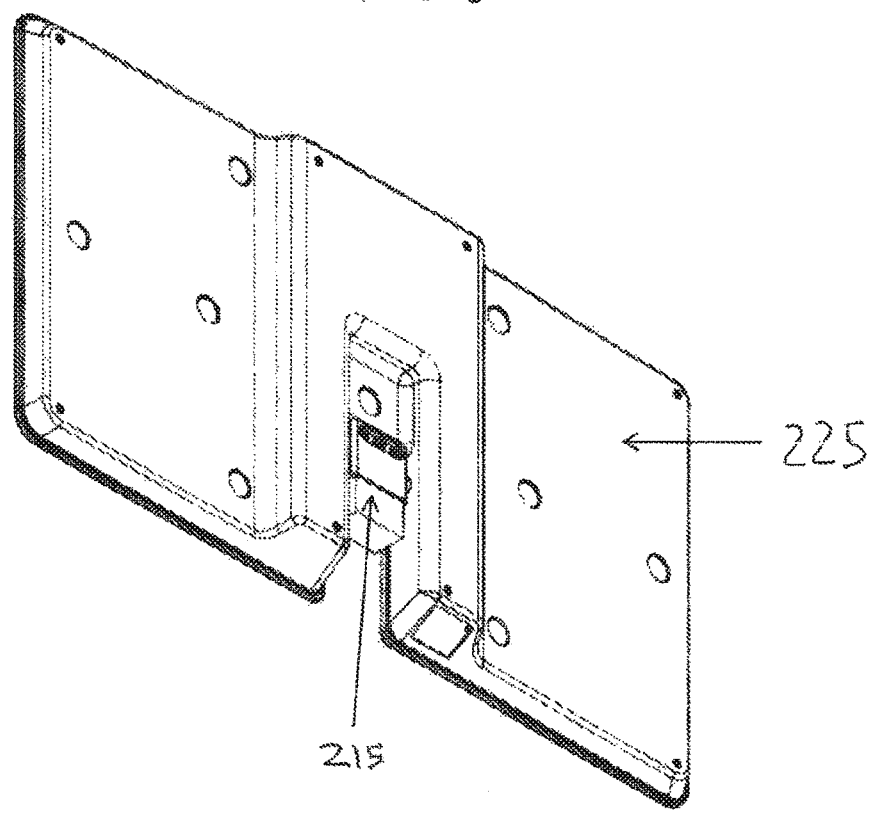
FIG. 7 is a bottom, perspective view of the light emitting head unit of FIG. 6.

FIG. 7 is a bottom, perspective view of the light emitting head unit 210.

Figure 8:
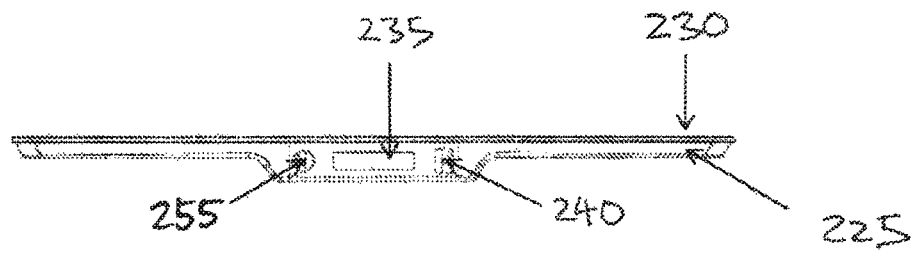
FIG. 8 is a front view of the light emitting head unit of FIG. 6.

FIG. 8 is a front view of the light emitting head unit 210.

The light emitting head unit or phototherapy device 210 may be used in conjunction with the mounting structure 120 described above. The light emitting head unit or phototherapy device 210 may be attached to the movable stand or mounting structure 120 via a tilt-mechanism 215 that can allow one-handed operation and automatically locks in place with a range of motion from 0 to 90 degrees, with a mechanical stop at 0 degrees.

The phototherapy device 210 comprises at least one high intensity light emitting diode (LED) 220 to emit a range of light wavelengths that corresponds to the peak absorption spectra for bilirubin (400 nm to 520 nm and preferably 430 nm to 490 nm and more preferably 445 nm to 475 nm). LEDs 220 that emit other light wavelengths useful in treating jaundice can also be used. The phototherapy device 210 may also comprise LEDs having an emission range of about 550 nm to 650 nm for use in observing the patient, wherein the LEDs may be operable together with or independently of the LEDs configured to provide the phototherapy.

The LEDs 220 may comprise high intensity LEDs. High intensity LEDs can use less power and have a longer lifespan than compact fluorescent and incandescent lights found in typical phototherapy devices in low-income countries. In areas with inconsistent electricity, the phototherapy devices 210 and 110 may be powered with a battery backup. The increased intensity and efficiency of the LEDs used in the devices 210 and 110 often mean that only a small number of LEDs are necessary to provide irradiance levels that meet American Academy of Pediatrics guidelines (>30 W/cm$^2$/nm).

Figure 9:
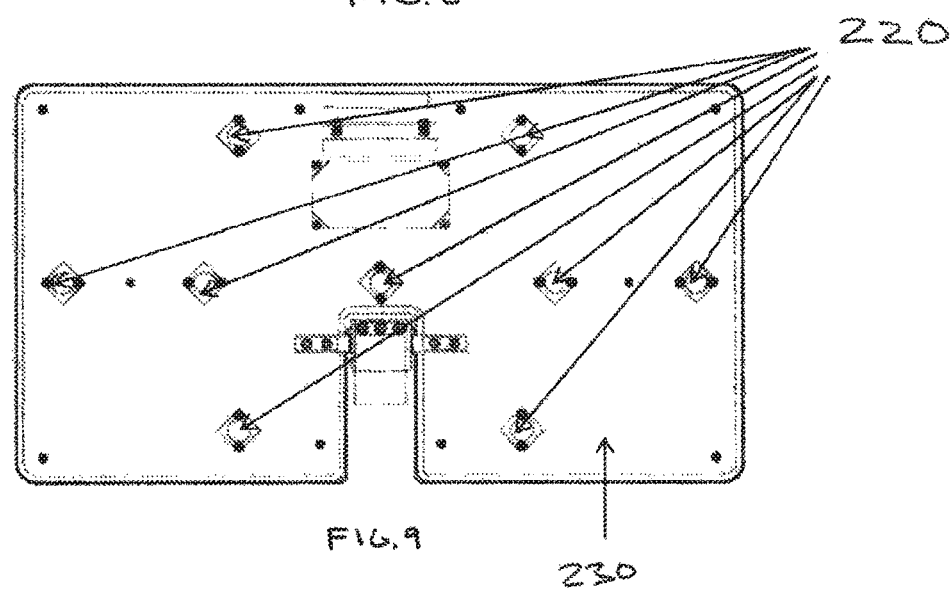
FIG. 9 is a bottom view of the light emitting head unit of FIG. 6 with its half-shell housing removed.

FIG. 9 is a bottom view of the light emitting head unit 210 with its half-shell housing 222 removed.

Figure 10:
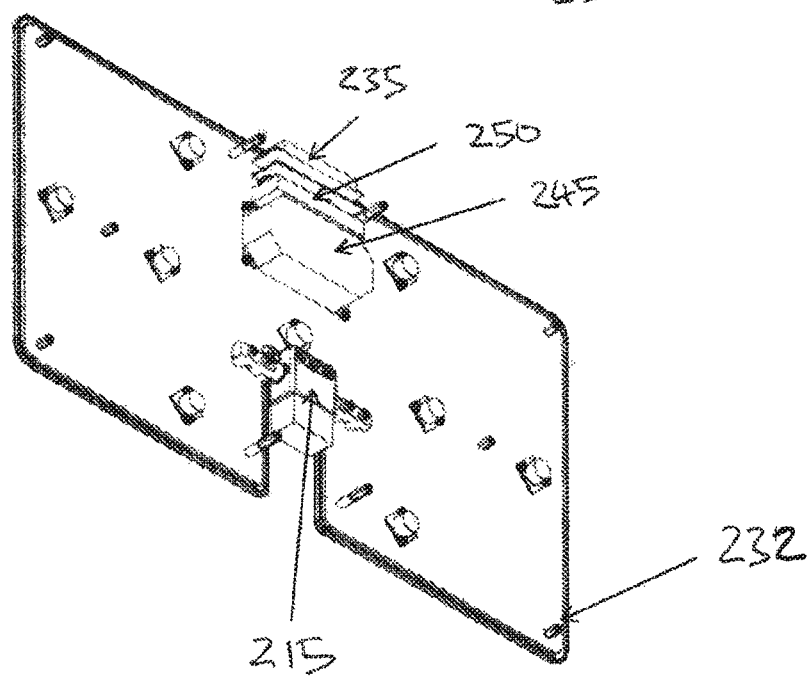
FIG. 10 is a bottom, perspective view of the light emitting head unit of FIG. 6 with its half-shell housing removed.

FIG. 10 is a bottom, perspective view of the light emitting head unit 210 with its half-shell housing 222 removed.

Figure 11:
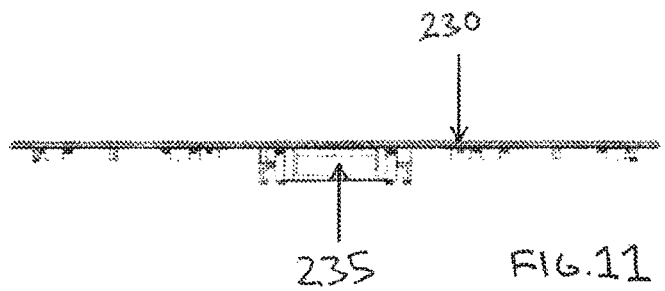
FIG. 11 is a front view of the light emitting head unit of FIG. 6 with its half-shell housing removed.

FIG. 11 is a front view of the light emitting head unit 210 with its a shell housing 222 removed.

Within the housing assembly and as illustrated in FIG. 9, the LEDs 220 are arranged in an array 225 in which groups of LEDs 220 are placed on different current strings. The multiple current strings allow for independently adjustable currents through one or more of resistor replacement and pulse-width modulation (PWM). The power or current input to the LED strings can also be automatically adjusted based on the measured distance between the light source and the treatment surface. The distance between the light source and the treatment surface may be measured by a distance meter integrated with or coupled to the phototherapy device or to a mounting structure attached to the phototherapy device. The distance meter may comprise a sensor, such as art optical range finder, to detect the distance between the phototherapy device and the treatment surface of the patient. Each LED 220 in the array is paired with focusing lenses at a variety of rotated angles. In preferred embodiments and as seen in FIGS. 6, 7, 9 and 10, the LEDs 220 are arranged in a non-uniform, highly unique pattern 225, wherein the number of LEDs 220 may vary. The LEDs are strategically configured to produce uniform doses of radiation to the surface of the treatment subject over a vertical distance range of 25-45 cm. Over this range and an emission range of 400 nm to 520 nm, the light output does not exceed 65 W/cm$^2$/nm, a dose thought to be potentially dangerous to premature infants. The unique configuration 225 of the LEDs 220 enables the phototherapy unit to be maximally efficient, with over 70% of the light output hitting the 25 cm×50 cm treatment surface at a treatment distance of 35 cm.

The array of LEDs 225 is typically fixed and mounted on a support structure comprising a heat-conductive metal plate 230, which can act as an external backing, mechanical infrastructure, and passive heat sink. The support structure may be made of one or more of copper, aluminum, ceramic, or other highly heat conductive material. In preferred embodiments, the support structure is a metal plate 230 made of aluminum. Because the heat-conductive metal plate 230 can eliminate the need for a fan to cool the light source, noise can be decreased and internal dust buildup minimized. Thus, these preferred embodiments can be easy to clean in low-resource environments. The elimination of the fan can also remove one of the most likely components to fail during a phototherapy unit's lifetime and can remove the need to purchase replaceable air filters. As illustrated in FIGS. 6-9, the array of LEDs 225 can be covered by a half-shell housing 222 that can be mechanically fastened to the metal plate such as with supports or engagement elements 232 as shown in FIG. 10. The half-shell 222 can be made of a variety of polymers and has circular cutouts over each LED lens to allow the light source to shine through. The diameter of the cutouts corresponds to that of the lens.

The phototherapy device 210 can also comprise a programmable control system or processor 250 that outputs characters to a display 235, which may comprise a contrast-adjustable liquid-crystal (LCD) display. A power supply 245 may provide power to one or more of the processor 250, the display 235, and the array of LEDs 225. A microcontroller in the processor 250 can allow the user to fluidly move through multiple intensity settings and reset the patient treatment time at any moment. The microcontroller can also run two semi-hidden modes: data mode and setup mode. The data mode can allow the user to scroll through the following: the device serial number, the number of patient therapy time resets, the total hours the unit has been on, the most recent light meter reading, and a checksum that can be used to verify whether the previous data points were correctly interpreted when input into a peripheral data collection form. As shown in FIG. 8, a settings adjustment button 255 adjacent to the display 235 may be provided to adjust the above settings and modes.

The setup mode can allow a repair technician or a manufacturing employee to adjust the baseline PWM for the LED strings at each power setting, to erase the stored data, to input the serial number, to set the time and date, to adjust the contrast of the LCD display 235, and to view the five most recent events. Every event may be stored on internal memory on the circuit board of the processor 250 and can be accessed through an internal connector or through an external SD card slot. These events can all be time-stamped and may include turning the unit on/off, plugging the unit into wall power, unplugging the unit from the wall power, the tilted angle of the unit taken at pre-programmed time intervals, the internal temperature of the unit at pre-programmed time intervals, readings from the peripheral light meter, resets to the patient therapy time, and the duration of brown-outs.

When a brown-out occurs, the microcontroller of processor 250 may measure the duration of each brown-out, and if the power outage duration is less than the programmed cut-off time, the unit may return to its previous status without user input required. The processor can detect loss of power and back up operating state, usage data, and other information.

An accelerometer on the processor can detect the tilt angle of the light emitting head unit. Using PWM, software on the processor can use a customized curve to increase or decrease the power or current supplied to the array of LEDs 225 based on the accelerometer inputs, in order to maintain a constant irradiance footprint at the treatment surface.

Since light output of the LEDs will likely diminish over time, the software on the processor can adjust the PWM of the current driver to discretely increase the power or current supplied to the array of LEDs 225 as the total light hours increase. This can compensate for the natural decay of the LED output and can enable the phototherapy unit 210 to provide more constant light output and maintain effective treatment irradiance over a longer lifetime.

Operational parameters from the processor are communicated to the user via a display screen 235. In its preferred embodiment and as illustrated in FIGS. 8 and 11, the display screen 235 comprises an alphanumeric LCD. To turn on the phototherapy unit, a user may flip up an ON switch 240 next to the display screen 235. The ON switch 240 can be in electronic communication with the display screen 235 such that the latter prompts the user to configure usage settings prior to light therapy. When the unit 210 is switched on, the user can be prompted to record whether this is a "new patient" or "old patient." The user may make a selection before the LEDs 220 output light. In general, settings may be configured with a button or other functional solutions next to the display screen 235. Flipping down the ON switch 240 terminates light therapy.

Figure 12:
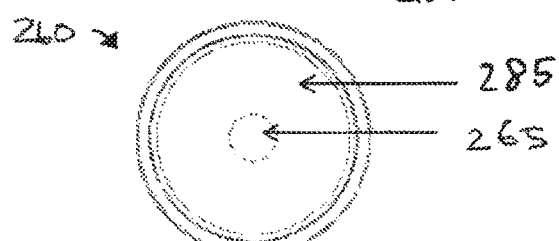
FIG. 12 is a top view of a light meter for use with the light emitting head unit of FIG. 6.

FIG. 12 is a top view of a light meter 260 for use with the light emitting head unit 210.

Figure 13:
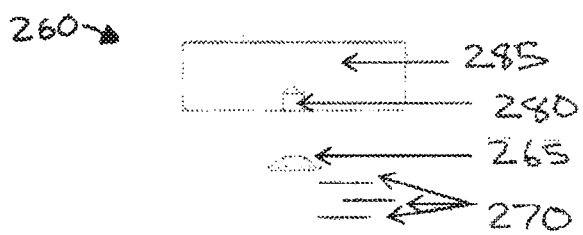
FIG. 13 is an exploded, side view of the light meter of FIG. 12.

FIG. 13 is an exploded, side view of the light meter 260.

Figure 14:
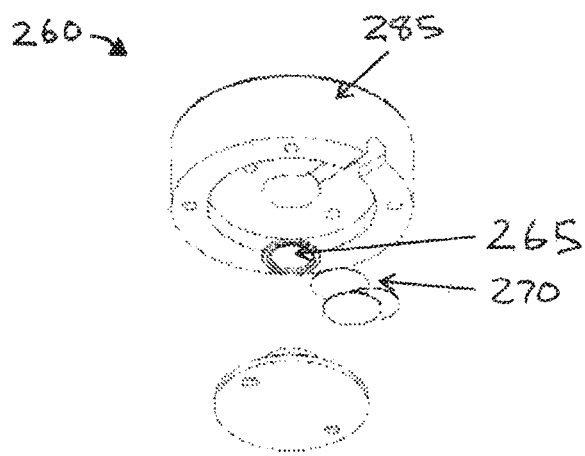
FIG. 14 is an exploded, bottom perspective view of the light meter of FIG. 12.

FIG. 14 is an exploded, bottom perspective view of the light meter 260.

On a lateral side of the device 210 may be a connector for a light meter accessory 260. The light meter 260 can be used to measure the irradiance of the array of LEDs 225. In preferred embodiments and as illustrated in FIGS. 12-14, the light meter 260 comprises a light meter housing 285, a light sensor 265, and a stack of filters 270 that can be combined to create a transmission spectrum nearly identical to the peak absorption spectrum of bilirubin. The light sensor 265 can output voltage that can then be converted into an irradiance value given the specific calibration curve of the device 210. This calibration curve can be stored on the circuit board 275 of the light meter 260 and can be added during manufacturing. Each unit 210 can have a slightly different calibration curve.

The detachable light meter 260 can store its own calibration data but may require an external LCD and circuit to display its measurements. The light meter 260 can be integrated with the processor 250 and LCD display 235 of the phototherapy unit 210 with a connector port 280, but can be moved and used on multiple devices. The outputs of the light meter 260 can be read by the processor 250 of the phototherapy unit 210 and can be translated to a character value displayed on the LCD 235. These values are then stored on the internal memory of the phototherapy unit 210.

When not in use, the light meter 260 can be stored in a vertical position on the lateral side of the phototherapy unit 210. In some embodiments, the phototherapy unit 210 may comprise a holster for storing the light meter, and/or a hook for placement of the light meter 260 which may have a hole in its handle portion for such a placement on the hook. Alternately or in combination, the light meter may be magnetically coupled to a surface of the phototherapy unit 210. An accelerometer sensor may be provided in the light meter 260 to detect when the meter 260 is in a horizontal position for measurements or vertical position for storage or other tilt or orientation of the light meter 260 or phototherapy unit 210. In the phototherapy unit 210, the processor 250 can auto-switch display modes to show measured irradiance when the light meter accessory 260 is horizontal, and can switch to normal operation when the light meter accessory 260 is vertical. Measurement and collection of usage data can be retrieved with a removable memory card through a compatible slot on a lateral side of the phototherapy unit 210.

In addition to interfacing with the display screen 235 on the phototherapy unit 210, the light meter accessory 260 can integrate with a smartphone and use a customized application to display its measurements. The light meter 260 may also have an option to be a standalone device that contains the circuitry to translate the sensor's voltage to an irradiance value displayed on an integrated LCD.

The processor of the phototherapy device may be programmed to calculate the dose of radiation provided to a patient during one or more treatments. The calculation may be based on one or more of the treatment parameters, including the area of the exposed treatment surface, the distance between the LEDs and the treatment surface, the total number of hours of use of the LEDs, and the intensity of the radiation provided. The calculated dose may be displayed on the LCD display screen.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A phototherapy system for the treatment of a subject, the system comprising:
   a phototherapy device comprising one or more LEDs and a processor to control the one or more LEDs, the one or more LEDs being configured to provide a uniform dose of radiation on a treatment surface of the subject over a distance range; and
   a light meter removably coupled to the phototherapy device and configured to measure the intensity of the radiation provided by the one or more LEDs, the light meter comprising:
      one or more filters configured to have a transmission spectrum corresponding to a target range of wavelengths,
      a light sensor configured to detect radiation and to output a voltage corresponding to the detected radiation, and
      a circuit board comprising a memory having a calibration curve stored thereon, wherein the circuit board further comprises a program configured to use the calibration curve to convert the voltage output of the light sensor into an irradiance value to be communicated to the processor of the phototherapy device.

2. The phototherapy system of claim 1, further comprising a display coupled to the processor of the phototherapy device, wherein the light meter comprises a connector port that removably couples the light meter to the phototherapy device, and wherein the irradiance value from the light meter is communicated to the processor of the phototherapy device and displayed by the display.

3. The phototherapy system of claim 1, wherein the processor is configured to adjust a power supplied to the one or more LEDs in response to one or more of an orientation of the phototherapy device, a distance between the one or more LEDs and the treatment surface, or a total number of hours of use of the one or more LEDs.

4. The phototherapy system of claim 1, wherein the phototherapy device comprises an accelerometer, and wherein the processor of the phototherapy device is configured to adjust a power supplied to the one or more LEDs in response to an orientation of the phototherapy device as provided by the accelerometer.

5. The phototherapy system of claim 1, wherein the processor of the phototherapy device is configured to adjust a power supplied to the one or more LEDs in response to a distance between the one or more LEDs and the treatment surface as provided by a distance meter coupled to or integrated into the phototherapy device or a mounting structure coupled to the phototherapy device.

6. The phototherapy system of claim 1, further comprising a support structure for coupling to and supporting the one or more LEDs, wherein the support structure is configured to absorb and dissipate heat generated by the one or more LEDs to minimize overheating without requiring the use of a fan.

7. The phototherapy system of claim 1,
wherein the light meter is further configured to detect an intensity of the radiation provided by the one or more LEDs for the treatment of the patient and to communicate the detected intensity to the processor; and
wherein the processor of the phototherapy device calculates the dose of radiation provided to the patient based on one or more of a size of the treatment surface, the distance between the one or more LEDs and the treatment surface, the total number of hours of use of the one or more LEDs, or the intensity of the radiation provided for the treatment of the patient.

8. The phototherapy system of claim 1, further comprising a display coupled to the processor of the phototherapy device, wherein the processor is configured to cause the display to display the detected intensity of the radiation provided by the one or more LEDs.

9. The phototherapy system of claim 1, wherein the light meter is configured to be stored in the phototherapy device.

10. The phototherapy system of claim 1, wherein the processor of the phototherapy device is configured to adjust a power supplied to the one or more LEDs to maintain the irradiance value at a desired range.

11. The phototherapy system of claim 1, wherein the phototherapy device comprises a cooling mechanism.

12. The phototherapy system of claim 11, wherein the cooling mechanism comprises one or more fans or heatsinks.

13. The phototherapy system of claim 11, wherein the cooling mechanism comprises a heat conductive metal plate.

14. The phototherapy system of claim 1, wherein the phototherapy device comprises a timer or memory coupled to the processor, and wherein the processor is configured to adjust a power supplied to the one or more LEDs in response to a total number of hours of use of the one or more LEDs recorded by the timer or memory.

* * * * *